(12) United States Patent
Fassi

(10) Patent No.: US 9,791,421 B2
(45) Date of Patent: Oct. 17, 2017

(54) ALIGNMENT AID SYSTEM FOR AN ULTRASONIC TRANSMITTER, AN ULTRASONIC DETECTOR ASSEMBLY AND AN ALIGNMENT METHOD

(71) Applicant: SCHNEIDER ELECTRIC INDUSTRIES SAS, Rueil Malmaison (FR)

(72) Inventor: Brice Fassi, Angouleme (FR)

(73) Assignee: SCHNEIDER ELECTRIC INDUSTRIES SAS, Rueil Malmaison (FR)

( * ) Notice: Subject to any disclaimer, the term of this patent is extended or adjusted under 35 U.S.C. 154(b) by 116 days.

(21) Appl. No.: 14/607,441

(22) Filed: Jan. 28, 2015

(65) Prior Publication Data

US 2015/0212050 A1     Jul. 30, 2015

(30) Foreign Application Priority Data

Jan. 30, 2014   (FR) ...................................... 14 50756

(51) Int. Cl.
*G01N 29/26*     (2006.01)
*G01N 29/30*     (2006.01)
(Continued)

(52) U.S. Cl.
CPC ........... *G01N 29/30* (2013.01); *G01N 29/223* (2013.01); *G01N 29/44* (2013.01); *G01N 2291/103* (2013.01); *G01N 2291/106* (2013.01)

(58) Field of Classification Search
CPC ...... G01N 29/30; G01N 29/223; G01N 29/44; G01N 2291/103; G01N 2291/106
(Continued)

(56) References Cited

U.S. PATENT DOCUMENTS

| 3,969,926 A | * | 7/1976 | Walker | G01N 29/11 |
| | | | | 73/620 |
| 4,155,243 A | | 5/1979 | Elsner | |
| 8,473,239 B2 | * | 6/2013 | Specht | A61B 8/00 |
| | | | | 702/100 |

FOREIGN PATENT DOCUMENTS

DE   10 2011 050 051 A1   11/2012
JP       2002195986 A   *   7/2002

OTHER PUBLICATIONS

French Preliminary Search Report issued Oct. 22, 2014, in Patent Application No. FR 1450756, filed Jan. 30, 2014 (with English Translation of Category of Cited Documents).

* cited by examiner

*Primary Examiner* — Helen Kwok
*Assistant Examiner* — Nashmiya Fayyaz
(74) *Attorney, Agent, or Firm* — Oblon, McClelland, Maier & Neustadt, L.L.P.

(57) ABSTRACT

There is provided an alignment aid method of an ultrasonic transmitter implemented by means of an alignment aid system. The alignment aid system includes a receiver including a plurality of transducers each configured to receive an ultrasonic wave and convert it into a respective signal, and a processing unit configured to digitally process all the signals coming from the transducers, at least part of the transducers being arranged so as to form a first continuous row of transducers. The system also includes an alignment control device communicating with the processing unit, the alignment control device being configured to supply an indication about the transducer(s) receiving a single ultrasonic wave transmitted by said transmitter along the first row of transducers so as to enable the transmitter to be aligned in relation to the receiver.

13 Claims, 2 Drawing Sheets

(51) Int. Cl.
    *G01N 29/44* (2006.01)
    *G01N 29/22* (2006.01)
(58) Field of Classification Search
    USPC .......................................................... 73/1.82
    See application file for complete search history.

ALIGNMENT AID SYSTEM FOR AN ULTRASONIC TRANSMITTER, AN ULTRASONIC DETECTOR ASSEMBLY AND AN ALIGNMENT METHOD

TECHNICAL FIELD

The invention relates to the field of ultrasonic object detection, and more precisely to the alignment of ultrasonic detectors enabling such a detection.

STATE OF PRIOR ART

Whether in the fields of logistic and transport or in that of automated industrial processes, it is not uncommon to employ ultrasonic detectors.

This type of detectors uses ultrasonic waves to detect the presence and/or the passage of an object being for example on a belt conveyor. In order to perform such a detection, these detectors comprise an ultrasonic transmitter and an ultrasonic receiver that can be independent of one another or in a single casing. In the latter configuration, the ultrasonic detector therefore acts both as a transmitter and a receiver.

Indeed, these ultrasonic detectors can operate according to three different configurations.

According to a first configuration, generally in a single casing, the ultrasonic detector transmits, continuously or pulse-wise, ultrasonic waves in the direction of a passage area of the object to be detected. Upon the passage of the object, the latter intercepts the ultrasonic waves and reflects part of them in the direction of the detector. Thus, in this first configuration, it is the detection of waves reflected by the object to be detected which allows the detection of the latter.

In a second configuration, generally in a single casing, depicted in FIG. 1, the detector 110 also transmits continuously or pulse-wise ultrasonic waves 111 in the direction of a passage area of the object to be detected. Beyond the passage area of the object to be detected and on the path of the ultrasonic waves, a reflector 120 is provided, such as a wall arranged to reflect the ultrasonic waves in the direction of the detector 110 so as to return said ultrasonic waves towards the detector 110. Thus, in the absence of the object to be detected, the reflector 120 reflects the ultrasonic waves 111 in the direction of the detector 110. In this second configuration, the passage of the object to be detected is detected when the object intercepts through its passage the ultrasonic waves 111. In this second configuration, it is therefore the modification or the interruption of the detection by the receiver of the reflected waves which allows the detection of the object to be detected.

In a third configuration, the transmitter and the receiver are independent and separated from each other. The transmitter transmits ultrasonic waves (continuously or pulse-wise) in the direction of the passage area of the object to be detected. The receiver is provided on the path of the ultrasonic waves beyond the passage area of the object to be detected. Thus, in the absence of the object to be detected, the receiver receives the ultrasonic waves. The object to be detected, during its passage, intercepts the ultrasonic waves and thus prevents their detection by the receiver. Therefore, it is also here the modification or the interruption of the detection of the ultrasonic waves by the receiver which allows the detection of the object to be detected.

For the sake of concision, it is meant thereafter and in the remainder of this document, by the transmitter of an ultrasonic detector, either the transmitting part of the latter when it is a single casing (particularly the first and second configurations), or the transmitter as such when the detector comprises an independent transmitter and an independent receiver.

Whatever the configuration used for the ultrasonic detection, the positioning of the detector transmitter is essential.

Indeed, in the first configuration, it is necessary that the positioning of the transmitter, which is defined by its orientation and its position in space, with respect to the reflecting face of the object to be detected should be perfectly controlled in order to ensure that a sufficient part of the ultrasonic waves is reflected in the direction of the receiving part of the detector. In the second and third configurations, it is the positioning, more precisely the orientation and the position, of the transmitter with respect to the reflector and/or the receiver which must be perfectly controlled. An incorrect orientation can, in both configurations, prevent any detection and therefore any operation of the detector.

Above and in the remainder of this document it is meant by orientation and position respectively of a transmitter with respect to a reference frame, such as a reflector or a receiver, the angle of the ultrasound transmitting direction of the transmitter with respect to said reference frame and the position in space of the transmitter with respect to the same reference frame, respectively. The positioning adjustment of a transmitter therefore corresponds both to the orientation and position adjustment of the transmitter.

The positioning adjustment of the transmitter is commonly referred to as alignment of the transmitter. The purpose indeed is to align the transmitting beam with respect to a reference frame.

This alignment is generally performed by trial and error by searching the positioning of the transmitter which enables the intensity of the ultrasonic waves received by the receiver to be maximized (in the presence of the object to be detected for the first configuration and in the absence of the object to be detected for the second and third configurations).

Such a procedure is long and relatively ineffective. Indeed, as depicted in FIG. 1 for the second configuration, it is necessary to act both on the orientation (angle α) and the position (represented by the distance d) of the transmitter 110. It is therefore uneasy for the operator performing this procedure to efficiently discriminate the parameter on which it is necessary to act and to identify the direction in which it is necessary to vary this parameter. With such a procedure, the operator is thus not ensured to reach this maximization of the intensity of the received ultrasonic waves 111 and the achieved alignment remains coarse and imprecise.

In order to optimize this process of aligning the ultrasonic transmitters, it could be possibly considered using a group of ultrasonic receivers.

Such a group of receivers could comprise a plurality of receivers. Each receiver would comprise a transducer, having an ultrasound receiving surface, and a processing unit configured to process the signals coming from the transducer.

This group of receivers should then be positioned, according to the configuration type of the ultrasonic detector, either opposite the passage area of the objects to be detected (the first configuration), or at the location of the reflector/receiver (the second and third configurations). Thus, by implementing ultrasound transmission by the transmitter, it should be possible to identify the receiver(s) of the group of receivers receiving the ultrasounds. According to the thus stimulated receiver(s), it should be possible to detect an alignment problem of the transmitter in relation either to the passage of the objects to be detected (the first configuration), or of the reflector/receiver (the second and third configurations) and to identify the direction along which the receiver is misaligned.

Thus, with such a group of receivers, the operator should be able to use the identified direction to modify one of both parameters among the orientation and the position of the transmitter and to achieve an alignment more rapidly than with the already explained trial and error method. However, due to the significant space between the receivers of the group, this indication would remain coarse and it would then still be difficult with such a group of receivers to perfectly optimize the alignment of the detector.

DISCLOSURE OF THE INVENTION

The object of the invention is to provide an alignment assistance of ultrasonic transmitters which enables a facilitated and improved alignment with respect to an alignment which could be performed using a group of receivers such as considered above.

To that end, the invention relates a method for aligning a transmitter by means of an alignment aid system, the alignment system comprising:
  a receiver comprising a plurality of transducers each adapted to receive an ultrasonic wave and to convert it into a respective signal, and a processing unit configured to process all the signals coming from the transducers, at least part of the transducers being arranged so as to form a first continuous row of transducers,
  an alignment control device arranged to communicate with the processing unit, the alignment control device being configured to supply an indication about the transducer(s) of the first row receiving said ultrasonic wave transmitted by said transmitter so as to enable the transmitter to be aligned in relation to the receiver,
  the method comprising the following steps of:
  positioning the receiver at a location, such as the one of a reflector, with respect to which the transmitter must be aligned,
  transmitting by the transmitter a single ultrasonic wave,
  receiving the ultrasonic wave by the transducers and converting into signals,
  processing by the processing unit the signals coming from the transducers,
  supplying by the alignment control device an indication about the detection of the single ultrasonic wave transmitted by the transmitter along the first row so as to enable the transmitter to be aligned in relation to the receiver.

Such a method allows, thanks to the arrangement of the transducers as a continuous row of transducers, the easy identification of the direction according to which along the row it is necessary to modify the positioning of the transmitter, this with a greater accuracy than would be possible with a method using a group of receivers. Indeed, the spacing between the transducers being minimum, the identification of the transducer receiving for the most part the ultrasonic wave is more accurate and therefore the alignment of the transmitter is more precise.

Furthermore, in this method, the use of transducers sharing the same processing unit allows the use of small size elementary transducers having therefore a significant density. Thus, such a method allows a discrimination of the wave form received along the first row of transducers, the wave being received by several transducers. Such a discrimination allows the identification of the parameter which must be acted upon among the orientation and the position of the transmitter in order to align the latter. Indeed, an incorrect orientation of the transmitter leads to an asymmetry of the received wave unlike an incorrect position of the latter.

Furthermore, the signals of the transducers being processed by the same processing unit and therefore identically processed and during a same processing cycle, comparing of the transmitted power to each transducer by the ultrasonic wave that stimulates it is immediate. Shifts that could be brought about by the use of processing units proper to each transducer/receiver are then avoided and a higher accuracy level can be achieved compared to the level obtained by a group of receivers.

It is meant above and in the remainder of this document by an arrangement of transducers so as to form a continuous row of transducers that two adjoining transducers along this row, except for the structural constraints (for example, related to the support of the transducers), have a space there between which is minimum.

The indication about the detection of the ultrasonic wave is either visual or audible.

During the processing step, the processing unit can analyze the peak intensity shift of the wave received on the surface of transducers, the symmetrical or asymmetrical shape of the same peak intensity and can identify the position and/or orientation error of the transmitter, and during the indication supplying step by the alignment control device, the indication can specify the positioning and/or the positioning error(s) of the transmitter identified by the processing unit.

Such methods allows a facilitated alignment of a transmitter.

The invention further relates to an alignment aid system for an ultrasonic transmitter adapted to transmit a single ultrasonic wave, the alignment aid system comprising:
  a receiver comprising a plurality of transducers each adapted to receive an ultrasonic wave and to convert it into a respective signal, and a processing unit configured to process all the signals coming from the transducers, at least part of the transducers being arranged so as to form a first continuous row of transducers,
  an alignment control device arranged to communicate with the processing unit, the alignment control device being configured to supply an indication about the transducer(s) of the first row receiving the single ultrasonic wave transmitted by said transmitter so as to enable the transmitter to be aligned in relation to the receiver.

Such an alignment aid system by allowing the implementation of the method according to the invention presents the advantages which are related thereto.

The alignment control device can be configured to supply the indication about the transducer(s) of the first row receiving said ultrasonic wave either visually or audibly.

Transducers can be arranged according to a two-dimension assembly along the first row and a second row so as to form a continuous surface of transducers, the alignment control device being configured to supply an indication about the transducer(s) receiving an ultrasonic wave transmitted by said transmitter on the surface.

Each transducer can have a receiving surface with a substantially rectangular, preferably square shape, on which said transducer receives the ultrasonic wave transmitted by said transmitter, the receiving surfaces being then arrangeable as rows and columns, the row direction corresponding to the first row of transducers and the column direction corresponding to the second row of transducers.

Such alignment aid systems each enable the transmitter to be aligned according to the combination of two directions, preferably the horizontal direction and the vertical direction, thus ensuring a perfect optimization of the alignment whatever the original positioning of the transmitter.

Above and in the remainder of this document, it is meant by "two-dimension assembly along the first row and a second row so as to form a continuous surface of transducers" that the space between two adjoining transducers along the first row and along the second row is, except for structural constraints (for example related to the support of the transducers), minimum.

A common casing can be provided, all the transducers being arranged in this common casing.

Such a common casing enables a compact receiver to be provided and allows a better integration of the transducers.

Each transducer can be an electromechanical transducer preferably selected from the piezoelectric transducers.

The alignment control device can exhibit a display area and a display controller configured to control the display of information regarding the positioning of the transmitter in relation to the receiving surface(s) receiving an ultrasonic wave, so as to supply the required indication for the alignment, this information preferably comprising the intensity of the ultrasonic wave received by each transducer.

Such a display area enables the operator to view rapidly the operations of orientation and position correction to be performed in order to align the receiver.

The alignment control device can be adapted to supply an audible or visual indication.

Such an indication is easily perceptible by the operator who has to perform the alignment of a transmitter.

Above and in the remainder of this document, it is meant by intensity of an ultrasonic wave received by each transducer, the total power or per surface unit, transmitted by the ultrasonic wave to said transducer. This power can for example be expressed in decibels or even arbitrary units, such as Hertz, as a function of the type of transducers and the type of processing unit.

The processing unit can be configured to analyze the intensity of the ultrasonic wave received by each transducer on the surface of transducers so as to identify the positioning of the transmitter, a shifted symmetrical peak intensity being identified as a position error of the transmitter, an asymmetrical peak intensity being identified as an orientation error of the transmitter, the display controller of the alignment control device being configured to control the display of the positioning indications of the transmitter identified by the processing unit.

The display controller of the alignment control device can be further configured to control the display of the displacement and orientation indications to be applied to the transmitter in order to perform the alignment.

Such a processing unit and such an alignment control device enable the operator to be guided during the alignment of the transmitter thus offering a particularly efficient alignment.

The invention further relates to an ultrasonic detector assembly comprising at least an ultrasonic transmitter and an alignment aid system according to the invention.

Such an ultrasonic detector assembly allows an optimized detection to be provided, such an assembly taking advantage of the improved alignment provided by an alignment aid system according to the invention.

The ultrasonic transmitter can be an ultrasonic detector adapted to transmit an ultrasonic wave and to detect the reflection of the latter wave on a surface, such as the one of an object to be detected or the one of a reflector.

The receiver of the alignment aid system can also act as an ultrasonic detector upon detecting an object to be detected, the receiver in this configuration receiving the ultrasonic wave transmitted in the absence of an object to be detected.

Such an ultrasonic detector assembly enables a quick realignment of the transmitter. Indeed, the receiver remaining in place during the use of the detector, there is no need to displace the receiver to realign the transmitter.

BRIEF DESCRIPTION OF THE DRAWINGS

The present invention will be better understood upon reading the description of exemplary embodiments, given purely by way of example and in no way limiting, with reference to the accompanying drawings in which.

Identical, similar or equivalent parts of the different figures bear the same reference numerals in order to facilitate switching from one figure to another.

The different parts represented in the figures are not necessarily drawn to a uniform scale, in order to make the figures more legible.

DETAILED DISCLOSURE OF PARTICULAR EMBODIMENTS

Figure 1:
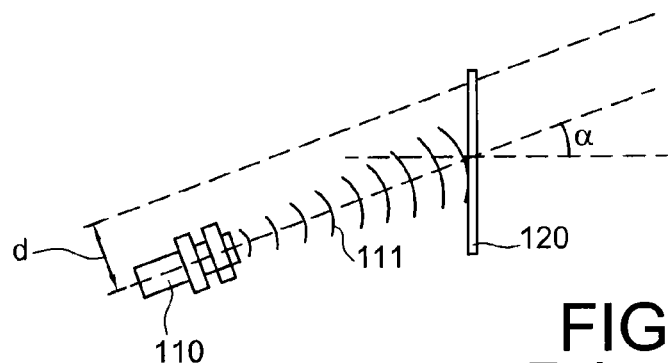
FIG. 1 depicts an exemplary detector having a disorientation of the angle $\alpha$ and a shift by the distance d.
Figure 2:
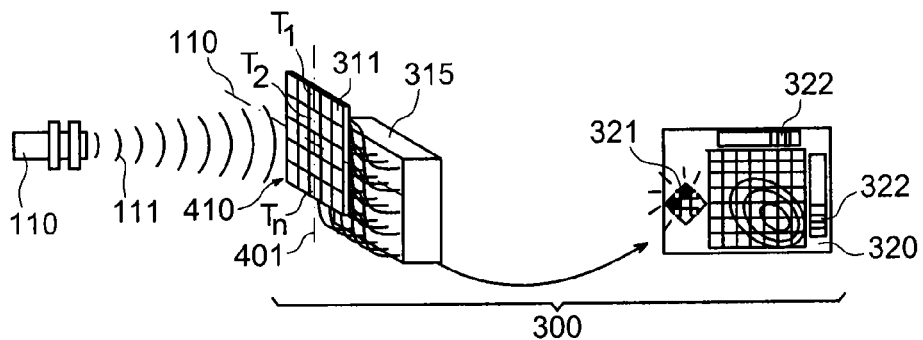
FIG. 2 depicts in operation an alignment aid system for a transmitter according to the invention.

FIG. 2 depicts an alignment aid system 300 according to the invention during the alignment of an ultrasonic transmitter 110 of an ultrasonic detector such as previously described.

Such an alignment aid system 300 comprises an ultrasonic receiver 310 and an alignment control device 320. The receiver 310 is intended to be placed at a location, such as the one of a reflector, with respect to which a transmitter 110 must be aligned.

The receiver 310 comprises:
  a plurality of transducers T1, T2 and Tn each adapted to receive an ultrasonic wave 111 and to convert it into a respective signal V1, V2, and Vn.
  a processing unit 315 configured to process all the signals V1, V2, Vn coming from the transducers T1, T2, Tn.

In this embodiment, each transducer T1, T2, Tn has a square shaped receiving surface 311. In this way, the receiving surfaces 311 are arranged according to a configuration of a two-dimension matrix so as to form a continuous surface 410 of transducers. Thus, the receiving surfaces 311, and therefore the transducers T1, T2, Tn themselves, are arranged according to a two-dimension assembly along a first and a second direction. The receiving surfaces 311, and therefore the corresponding transducers T1, T2, Tn, are arranged in rows and columns, according to the first and the second direction, respectively.

Thus, the transducers T1, T2, Tn, along the first direction, form a first continuous row 401 of transducers T1, T2, Tn. Similarly the transducers T1, T2, Tn, along the second direction, form a second continuous row 402 of transducers T1, T2, Tn. Therefore, the receiving surfaces 311 then form a continuous surface 410 of transducers T1, T2, Tn.

Of course, the alignment continuity of the transducers of the first and second rows described above is meant within the limit of the structural constraints of the receiver particularly related to the support of the transducers, the space between two adjoining transducers along one of these two rows being minimum.

Transducers T1, T2, Tn are each adapted to convert the ultrasonic waves 111 received on their receiving surface 311 into an electrical signal V1, V2, Vn. Transducers T1, T2, Tn can thus be electromechanical transducers such as piezoelectric transducers.

Figure 3:
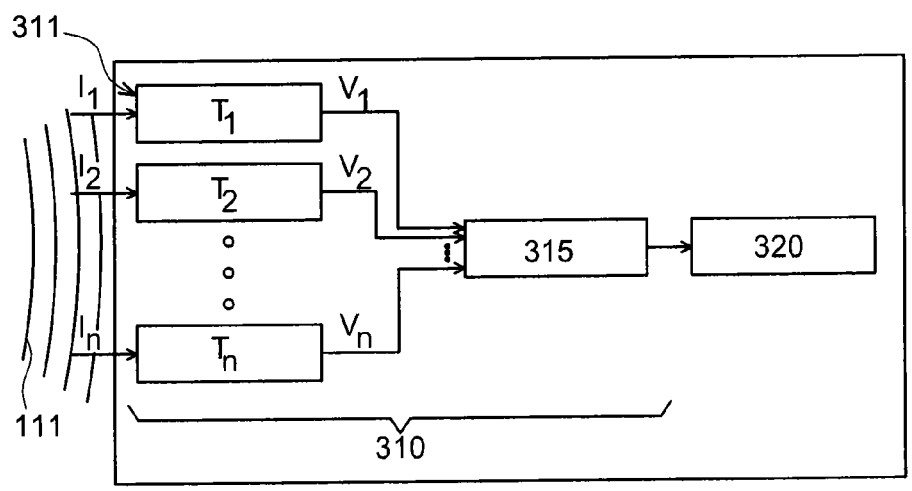
FIG. 3 depicts a block diagram of an alignment aid system according to the invention.

Transducers T1, T2, Tn are, as depicted on the bloc diagram of FIG. 3, each connected to the processing unit 315. The processing unit 315 is configured to process all the signals V1, V2, Vn coming from the transducers T1, T2, Tn and to determine, from these signals V1, V2, V3, the intensity of the ultrasonic wave 111 received by the corresponding transducers T1, T2, Tn.

The processing unit 315 enables for each transducer T1, T2, Tn an intensity of the ultrasonic wave received by said corresponding transducer to be determined, for example, at the power transmitted to said transducer in decibels or even arbitrary units, such as Hertz. Thus, the processing unit 315 enables the transducer(s) T1, T2, Tn receiving the greatest ultrasonic intensity to be defined.

The processing unit 315 is connected to the alignment control device 320 and is configured to transmit to the alignment control device 320 the processing result of the signals V1, V2, Vn coming from the transducers T1, T2, Tn.

The alignment control device 320 has a monitor forming a display area and a display controller adapted to control the display of the latter. The display controller is adapted to have the two-dimension distribution of the intensity received by the transducers T1, T2, Tn displayed on the monitor. The display controller also enables indications 321, 322 about the direction and the orientation in which the transmitter 110 must be displaced to be aligned on the monitor.

In use, such an alignment aid system 300 for a transmitter 110 is implemented according to a method comprising the following steps:
positioning the receiver 310 at a location, such as the passage area of the object to be detected, the location of the reflector 120 or even of a receiver, with respect to which the transmitter must be aligned,
transmitting by a transmitter 110 a single ultrasonic wave 111,
receiving by the transducers T1, T2, Tn the ultrasonic wave 111 and converting into signals V1, V2, Vn,
processing by a processing unit 315 the signals V1, V2, Vn coming from the transducers T1, T2, Tn,
supplying by the alignment control device 320 an indication about the detection of the single ultrasonic wave transmitted by the transmitter 110 on the surface 410 of transducers, and particularly, along the first row 401, so as to enable the transmitter 110 to be aligned in relation to the receiver.

The indication supplied by the control device depicted in FIG. 3, corresponds to the display of the two-dimension distribution of the intensity received by the different transducers T1, T2, Tn.

FIGS. 4 a)-d) depict examples of alignment of a transmitter 110 in the case of a receiver 310 having a single row of transducers, the first row 401, along which these transducers T1, T2, Tn are aligned. These FIGS. 4a)-4d) associate, on the lower part thereof, each alignment example with the intensity variation along the first row such as it is processed by the processing unit 315.

Figure 4A:
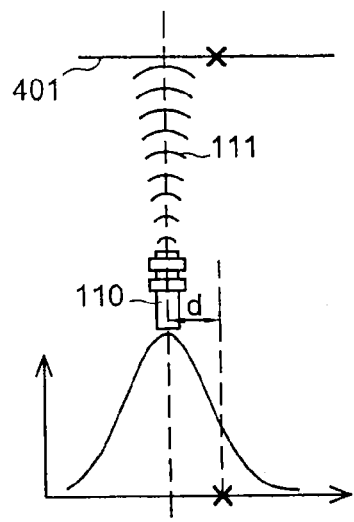
FIGS. 4A-4D depict several examples of alignment of a transmitter associated with the graphics of the intensity measures processed by the corresponding processing unit.

FIG. 4a) depicts an exemplary transmitter 110 shifted by a distance d. The measures processed by the processing unit 315 show a perfectly symmetrical peak intensity shifted by the distance d. Such a shift without an asymmetry is characteristic of a position error.

Figure 4B:
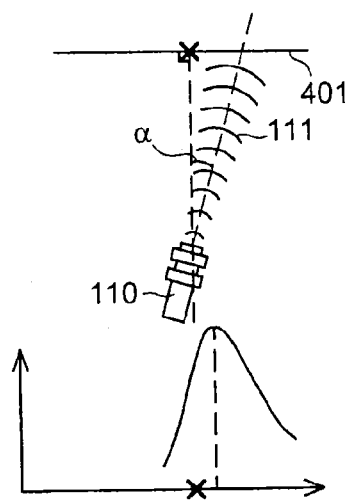

FIG. 4b) depicts an exemplary transmitter 110 having an angle α disorientation. The measures processed by the processing unit 315 show a peak intensity which is asymmetrical and off-centered due to the disorientation. Such an asymmetry of the peak intensity associated with such a shift is characteristic of an orientation error.

Figure 4C:
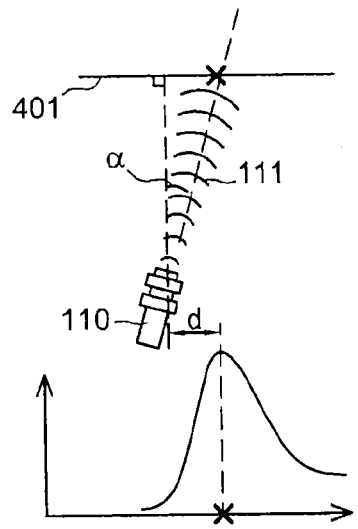

FIG. 4c) depicts an exemplary transmitter 110 having a disorientation of an angle α and a shift by a distance d. The measures processed by the processing unit 315 show a peak intensity which, even if it seems properly centered, has a marked asymmetry characteristic of an orientation error. The fact that the peak intensity has a shift which is different from the one related to the disorientation only of the transmitter 110, which, in this figure, compensates for the disorientation shift, is therefore characteristic of a position error of the transmitter 110, coupled to an orientation error of the transmitter 110.

Figure 4D:
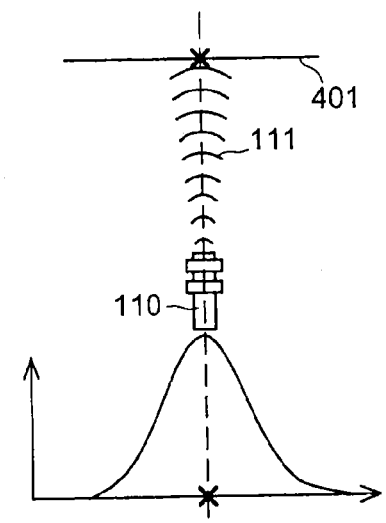

FIG. 4d) depicts an exemplary aligned transmitter 110. In this case, the ultrasonic waves are received in the center of the receiver and only the central transducers T1, T2, Tn are stimulated with an intensity which gradually decreases by moving away from the center of the receiver 300. In this example the peak intensity is therefore symmetrical and centered, which is characteristic of a proper alignment of the transmitter.

Thus with an alignment aid system 300 according to the invention, it is possible to discriminate an orientation error from a position error and even to decorrelate these two error types when a transmitter 110 accumulates these two error types.

According to a particularly advantageous possibility of the invention, the processing unit can be adapted to identify according to the principle explained above the parameter(s) to be modified in order to align the detector and the direction along which the parameter must be modified. This information can be transmitted to the alignment control device 320 so that the latter displays the indications to facilitate the alignment of the transmitter 110.

According to this possibility, the processing unit 315 is configured to analyze the intensity variation of the single ultrasonic wave 111 along the surface 410 of transducers T1, T2, Tn so as to identify the positioning errors of the transmitter 110, a shifted symmetrical peak intensity being identified as a position error of the transmitter 110, an asymmetrical peak intensity being identified as an orientation error of the transmitter 110. The display controller of the alignment control device 320 is configured to control the display in order to display indications about the positioning error(s) of the transmitter 110 identified by the processing unit 315 and the means to correct it (them). Thus, in operation, as illustrated in FIG. 2, the monitor can display on a first area 321 the direction(s) along which the transmitter 110 must be shifted in order to correct its position and on a second area 322 the direction(s) along which the transmitter 110 must be turned in order to correct its orientation.

The alignment aid system 300 according to this possibility is implemented by a method according to which:
during the processing step, the processing unit 315 analyzes the peak intensity shift of the ultrasonic wave received on the surface 410 of transducers T1, T2, Tn and the symmetrical or asymmetrical shape of the same peak intensity and extract therefrom the position and/or orientation error of the transmitter 110, during the indication supplying step by the alignment control device 320, the indication specifies the positioning error(s) of the transmitter 110 identified by the processing unit 315.

According to a first alternative of the invention wherein the alignment aid system 300 is for aligning the transmitter 110 of a detector according to one of the first and second configurations (please refer to the state of prior art), the alignment aid system 300 can be part of an ultrasonic detector assembly. According to this first alternative, the detector assembly comprises the detector 110 which itself comprises a receiver and a transmitter in a single casing, and an alignment aid system 300 according to the invention. In such a configuration, the alignment aid system 300 is only implemented during the alignment of the transmitter/detector 110.

According to a second alternative of the invention wherein the alignment aid system 300 is for aligning a transmitter 110 of a detector according to the third configuration (please refer to the state of prior art), the alignment aid system can be part of an ultrasonic detector assembly. According to this second alternative, the receiver 310 of the alignment aid system 300 can also be implemented upon detecting the passage of an object to be detected and then acts as a receiver for the ultrasonic detector, the ultrasonic detector comprising no dedicated receiver. Such a detector assembly is particularly advantageous to allow a steady alignment of the transmitter 110, the receiver of the alignment aid system remaining in place during the operation of the detector.

According to this second alternative, it is also possible for the ultrasonic detector to comprise a dedicated ultrasonic receiver without departing from the scope of the invention. Of course, in this case, the receiver 310 is only set up when performing an alignment of the transmitter 110.

Of course, if in the above described embodiment the receiving surface 311 of each transducer T1, T2, Tn has a square shape, the shape of the receiving surface of one or more transducers can have another receiving surface shape without departing from the scope of the invention. Thus, one or more transducers T1, T2, Tn can for example have a rectangular or diamond shape or even curvilinear shape subject to such a form being compatible with the fact that at least part of the transducers is arranged to form a first continuous row of transducers.

According to a possibility wherein the shape of the receiving surface 311 of the transducers T1, T2, Tn is other than square, it may also be contemplated that the first and second rows form an angle other than an angle substantially equal to 90°. Thus in the case where the receiving surfaces have a diamond shape, the first and the second row can for example form an angle of 30° with respect to one another without departing from the scope of the invention.

If in the above described embodiment of the invention, the control device 320 comprises a monitor to supply the indications about the transducer(s) T1, T2, Tn receiving the single ultrasonic wave 111 transmitted by the transmitter 110, it is also possible, without departing from the scope of the invention, for the alignment control device to supply said indication by another means such as for example an audible system.

The invention claimed is:

1. A method for aligning an ultrasonic transmitter by means of an alignment aid system, the alignment aid system comprising:
   a receiver comprising a plurality of transducers each configured to receive a single ultrasonic wave transmitted by the ultrasonic transmitter and to convert the single ultrasonic wave into a respective signal, and a processing unit configured to process all signals coming from the plurality of transducers, at least part of the plurality of transducers being arranged so as to form a first continuous row of transducers, the receiver being distinct from the ultrasonic transmitter and being disposed at a position that is different than that of the ultrasonic transmitter; and
   an alignment control device arranged to communicate with the processing unit, the alignment control device being configured to supply an indication regarding transducers of the first continuous row of transducers receiving the single ultrasonic wave transmitted by the ultrasonic transmitter so as to enable the ultrasonic transmitter to be aligned in relation to the receiver;
   the method comprising:
   positioning the receiver at a location with respect to which the ultrasonic transmitter must be aligned;
   transmitting, by the ultrasonic transmitter, the single ultrasonic wave;
   receiving the single ultrasonic wave by the transducers of the first continuous row of transducers and converting into the signals;
   processing, by the processing unit, the signals coming from the transducers of the first continuous row of transducers; and
   supplying, by the alignment control device, an indication about a detection of the single ultrasonic wave transmitted by the ultrasonic transmitter along the first continuous row so as to enable the ultrasonic transmitter to be aligned in relation to the receiver.

2. The method for aligning the ultrasonic transmitter according to claim 1, wherein the indication about the detection of the single ultrasonic wave is either visual or audible.

3. The method for aligning the ultrasonic transmitter according to claim 2,
   wherein during the processing, the processing unit analyses a symmetrical or asymmetrical shape of a peak intensity of the single ultrasonic wave received by the transducers of the first continuous row of transducers and a symmetrical or asymmetrical shape of a peak intensity shift of said peak intensity, and identifies a position and/or orientation error of the ultrasonic transmitter, and
   wherein during the indication supplied by the alignment control device, the indication specifies a positioning and/or a positioning error(s) of the ultrasonic transmitter identified by the processing unit.

4. An alignment aid system for an ultrasonic transmitter configured to transmit a single ultrasonic wave, the alignment aid system comprising:
   a receiver comprising a plurality of transducers each configured to receive the single ultrasonic wave transmitted by the ultrasonic transmitter and to convert the single ultrasonic wave into a respective signal, and a processing unit configured to process all signals coming from the plurality of transducers, at least part of the plurality of transducers being arranged so as to form a first continuous row of transducers, the receiver being distinct from the ultrasonic transmitter and being disposed at a position that is different than that of the ultrasonic transmitter; and an alignment control device arranged to communicate with the processing unit, the alignment control device being configured to supply an indication regarding transducers of the first continuous row of transducers receiving the single ultrasonic wave transmitted by the ultrasonic transmitter so as to enable the ultrasonic transmitter to be aligned in relation to the receiver, said indication also regarding a detection of the single ultrasonic wave transmitted by the ultrasonic transmitter along the first continuous row so as to enable the ultrasonic transmitter to be aligned in relation to the receiver.

5. The alignment aid system according to claim 4, wherein the alignment control device is configured to supply the indication either visually or audibly.

6. The alignment aid system according to claim 4, wherein the plurality of transducers are arranged according to a two-dimensional assembly comprising at least the first continuous row of transducers and a second continuous row of transducers so as to form a continuous surface of transducers, the alignment control device being further configured to supply the indication regarding transducers of the first continuous row of transducers and the second continuous row of transducers receiving the single ultrasonic wave transmitted by said ultrasonic transmitter on the continuous surface of transducers.

7. The alignment aid system according to claim 6, wherein each transducer on the continuous surface of transducers comprises a receiving surface on which said each transducer receives the single ultrasonic wave transmitted by the ultrasonic transmitter, said each receiving surface having a substantially rectangular shape or a square shape and being arranged as rows and columns, a row direction corresponding to the first continuous row of transducers and a column direction corresponding to the second continuous row of transducers.

8. The alignment aid system according to claim 7, wherein the alignment control device exhibits a display area and a display controller configured to control display of information regarding positioning of the ultrasonic transmitter in relation to said each receiving surface receiving the single ultrasonic wave so as to supply said indication.

9. The alignment aid system according to claim 8, wherein the information comprises a peak intensity of the single ultrasonic wave received by said each transducer.

10. The alignment aid system according to claim 8, wherein the processing unit is further configured to analyze a symmetrical or asymmetrical shape of a peak intensity of the single ultrasonic wave received by said each transducer and a symmetrical or asymmetrical shape of a peak intensity shift of said peak intensity, where the symmetrical shape of the peak intensity shift is identified as due to a position error of the ultrasonic transmitter and an asymmetrical shape of the peak intensity shift is identified as due to an orientation error of the ultrasonic transmitter, and wherein the display controller is further configured to control display of positioning indications of the ultrasonic transmitter identified by the processing unit.

11. An ultrasonic detector assembly comprising at least one ultrasonic transmitter configured to transmit a single ultrasonic wave, and an alignment aid system for aligning the ultrasonic transmitter, said system being an alignment aid system according to claim 4.

12. The ultrasonic detector assembly according to claim 11, wherein the at least one ultrasonic transmitter is an ultrasonic detector configured to transmit the single ultrasonic wave and to detect a reflection of the single ultrasonic wave on a surface, said surface being a surface of an object to be detected or a surface of a reflector.

13. The ultrasonic detector assembly according to claim 11, wherein the receiver of the alignment aid system is configured to act as an ultrasonic receiver of the ultrasonic detector assembly upon detecting an object to be detected, the receiver of the alignment aid system being further configured to receive the single ultrasonic wave transmitted in an absence of the object to be detected.

\* \* \* \* \*